(12) United States Patent
Lehmann et al.

(10) Patent No.: US 9,302,915 B2
(45) Date of Patent: Apr. 5, 2016

(54) METHOD FOR PRODUCING POLYSILANE, POLYSILANE, AND SILICON CARBIDE PRODUCED THEREFROM

(71) Applicant: BJS CERAMICS GMBH, Gersthofen (DE)

(72) Inventors: Tobias Lehmann, Wernau (DE); Joahim Bill, Weil der Stadt (DE); Andreas Kienzle, Moettingen (DE)

(73) Assignee: BJS Ceramics GmbH, Gersthofen (DE)

( * ) Notice: Subject to any disclaimer, the term of this patent is extended or adjusted under 35 U.S.C. 154(b) by 0 days.

(21) Appl. No.: 14/595,361

(22) Filed: Jan. 13, 2015

(65) Prior Publication Data

US 2015/0122149 A1     May 7, 2015

Related U.S. Application Data

(63) Continuation of application No. PCT/EP2013/064840, filed on Jul. 12, 2013.

(30) Foreign Application Priority Data

Jul. 13, 2012    (DE) .......................... 10 2012 212 365

(51) Int. Cl.

| | | |
|---|---|---|
| C07F 7/08 | (2006.01) |
| C01B 31/36 | (2006.01) |
| C04B 35/571 | (2006.01) |
| C08G 77/60 | (2006.01) |
| C04B 35/80 | (2006.01) |
| C08K 7/10 | (2006.01) |

(52) U.S. Cl.
CPC ............... *C01B 31/36* (2013.01); *C04B 35/571* (2013.01); *C04B 35/806* (2013.01); *C07F 7/0809* (2013.01); *C08G 77/60* (2013.01); *C08K 7/10* (2013.01); *C04B 2235/483* (2013.01); *C04B 2235/5244* (2013.01); *C04B 2235/5264* (2013.01); *C04B 2235/6562* (2013.01); *C04B 2235/785* (2013.01); *C04B 2235/786* (2013.01)

(58) Field of Classification Search
CPC .............................. C07F 7/0809; C08G 77/60
See application file for complete search history.

(56) References Cited

U.S. PATENT DOCUMENTS

| | | | | |
|---|---|---|---|---|
| 2,563,005 | A * | 8/1951 | Clark ............... | 528/43 |
| 4,310,651 | A * | 1/1982 | Baney et al. .......... | 528/21 |
| 4,595,472 | A * | 6/1986 | Haluska ........... | 522/99 |
| 5,091,485 | A | 2/1992 | Noireaux et al. | |
| 5,204,380 | A | 4/1993 | Seyferth et al. | |
| 2009/0124781 | A1* | 5/2009 | Hein et al. ............... | 528/10 |
| 2009/0156775 | A1* | 6/2009 | Sakamoto et al. .......... | 528/30 |
| 2013/0011675 | A1 | 1/2013 | Clade et al. | |

FOREIGN PATENT DOCUMENTS

| | | |
|---|---|---|
| JP | 2000239391 A | 9/2000 |
| WO | 2011064174 A1 | 6/2011 |

* cited by examiner

*Primary Examiner* — Margaret Moore
(74) *Attorney, Agent, or Firm* — Laurence A. Greenberg; Werner H. Stemer; Ralph E. Locher

(57) ABSTRACT

A method for producing a polysilane includes a step of reacting (i) at least two silane monomers and (ii) at least one alkali metal. The silane monomers contain the following structural units: at least one aryl group, at least one alkyl group, at least one alkenyl group, and at least three halogen atoms. At least three of the halogen atoms are bonded to a silicon atom of one of the silane monomers.

6 Claims, No Drawings

METHOD FOR PRODUCING POLYSILANE, POLYSILANE, AND SILICON CARBIDE PRODUCED THEREFROM

CROSS-REFERENCE TO RELATED APPLICATION

This application is a continuation, under 35 U.S.C. §120, of copending international application No. PCT/EP2013/064840, filed Jul. 12, 2013, which designated the United States; this application also claims the priority, under 35 U.S.C. §119, of German patent application No. DE 10 2012 212 365.2, filed Jul. 13, 2012; the prior applications are herewith incorporated by reference in their entirety.

BACKGROUND OF THE INVENTION

Field of the Invention

The present invention relates to a method for producing a polysilane, to a polysilane obtained thereby, to a shaped silicon carbide ceramic, in particular a silicon carbide fiber, produced from the polysilane, to a composite material produced therefrom and also to its use.

Ceramic component parts are used in various technical fields, for example, in the electrical industry, in motor vehicle construction, in aircraft construction and in biomedical engineering. Silicon carbide (SiC) is frequently added to technical ceramics, in particular when they are designed for applications where the hardness and heat resistance of the material has to meet high expectations, as is the case for example with materials for aerospace applications, such as materials for an airplane turbine. Silicon carbide is a chemical compound in which every silicon atom links through covalent bonds to four carbon atoms arranged tetrahedrally about the silicon atom, and accordingly has a construction which corresponds to that of diamond. For this reason, silicon carbide is very similar to diamond in having an extraordinarily high level of hardness and an excellent level of high temperature resistance. Silicon carbide further also has a very high level of chemical resistance in that it is capable of withstanding attacks by chlorine, sulfur, oxygen and strong acids even at a comparatively high temperature. In order to still further enhance the mechanical properties and especially the fracture toughness of the material, there has recently been an increasing trend to use composite materials based on silicon carbide where fibers of silicon carbide are embedded in a matrix of silicon carbide. Materials of this type have outstanding properties and so are used, for example, for heat shields of spacecraft and for airplane turbines. Likewise desirable is the utilization of these materials in clutches and brake disks. They are, however, currently still too costly for such use.

Silicon carbide fibers are typically manufactured on an industrial scale via a Wurtz coupling, where an organohalosilane, such as dimethyldichlorosilane for example, is reacted with molten sodium metal to form a polydimethylsilane which is then thereafter converted into a polycarbosilane. This polycarbosilane is then melt spun into fibers, before the fibers thus obtained are first electron beam or oxygen cured and finally converted into silicon carbide fibers by pyrolysis.

However, the production method described above is disadvantageous in that it leads to silicon carbide fibers that include a high proportion of free carbon. This is excess carbon in that it is present in unbound form in the silicon carbide obtained. Such free carbon, however, is undesirable because it limits the service temperature of silicon carbide fibers in oxidative atmospheres, since it burns up at comparatively high temperatures to form carbon monoxide and carbon dioxide. To reduce the proportion of free carbon in silicon carbide materials it has already been proposed to admix the polysilane before pyrolysis with a sintering additive, for example aluminum or boron, or to calcine the silicon carbide after pyrolysis. However, these methods are costly and inconvenient. While the first variant, involving the addition of a sintering additive, requires a two-step pyrolysis instead of a one-step pyrolysis and also, on account of the addition of a sintering additive, has additional material requirements, the second variant requires an additional operation in the form of a calcining step. In addition any subsequent calcining/burning step involves the removal of the free carbon and so leads to a material having a comparatively high level of porosity. For these reasons, these two variants are very costly and inconvenient technically, temporally and personnelwise. Furthermore, at least in the case of the latter variant, the removal of free carbon during calcination may create dislocations that reduce the mechanical stability of the fibers. A further disadvantage of the methods described above is that, before spinning and before pyrolysis, the polysilane is first converted into a polycarbosilane, requiring a separate operation and the provision of a suitable reactor. For all these reasons, the aforementioned methods are unsatisfactory. There is accordingly a need for methods which without additional operations lead to silicon carbide having a nearly stoichiometric ratio of silicon to carbon, i.e., to silicon carbide having a ratio of silicon to carbon that is very close to 1.

U.S. Pat. No. 5,091,485 describes a method for producing polysilanes that are convertible into silicon carbide by heat treatment. That method comprises reacting at least one silane monomer of formula $R^1R^2SiCl_2$, where $R^1$ is a hydrogen atom or a hydrocarbon radical and $R^2$ is a vinyl radical, with at least one monochlorinated comonomer in the presence of molten sodium in an organic solvent to form a polysilane. The monochlorinated comonomer used may be an organic compound, for example a benzyl chloride or an organosilane of the formula $R^1{}_3SiCl$, where $R^1$ may be a hydrogen atom or a hydrocarbon radical. However, that method has the disadvantage that the polysilanes obtained therewith have a comparatively low molar mass and so are liquid at room temperature. For this reason, the polysilanes obtained have poor processability before conversion into silicon carbide. In particular, spinning these polysilanes into fibers and accordingly a subsequent conversion into silicon carbide fibers is only possible with unsatisfactory results, if at all. In addition, the method described in this printed publication gives rise to a comparatively high proportion of polysilanes that are insoluble in the organic solvents used during the reaction and workup. These insoluble polysilanes are separated off during the workup and purification steps, which are necessary before the conversion into silicon carbide in order to obtain a very pure polysilane as starting material, and this appreciably reduces the reaction yield. For example, products formed in the course of the reaction and generated in the form of a solid material, sodium chloride is an example, have to be separated off by filtration. The insoluble polysilane fractions remain in the filter cake, while the soluble polysilane fractions are a solute in the filtrate. Therefore, only the soluble polysilane fraction in the filtrate can be isolated and sent for further use, since any conceivable isolation of the insoluble fraction from the filter cake would be associated with too many additional operations and increased technical, temporal and personnel requirements.

SUMMARY OF THE INVENTION

It is accordingly an object of the invention to provide a method for producing polysilane and silicon carbide which overcomes the above-mentioned and other disadvantages of the heretofore-known devices and methods of this general type and which provides for a method that leads in a simple, quick and inexpensive manner to a polysilane with a comparatively high molar mass, with a comparatively high soluble fraction in the solvent used, with an excellent level of processability and also with a silicon-to-carbon ratio near the stoichiometric ratio of silicon carbide SiC.

With the foregoing and other objects in view there is provided, in accordance with the invention, a method for producing a polysilane, the method comprising:

reacting (i) at least two silane monomers and (ii) at least one alkali metal, the silane monomers containing the following structural units:
 at least one aryl group;
 at least one alkyl group;
 at least one alkenyl group; and
 at least three halogen atoms, wherein at least three of the halogen atoms attach to a silicon atom of one of the silane monomers.

This solution is based on the surprising finding that the step of reacting at least two silane monomers and one alkali metal, wherein the silane monomers contain the following structural units at least one aryl group, at least one alkyl group, at least one alkenyl group, and at least three halogen atoms, wherein at least three of the halogen atoms attach to a silicon atom of one of the monomers, results in a polysilane which has not only a comparatively high molar mass but at the same time also a high proportion of organic solvent soluble polysilane. On the contrary, this method leads in particular also to a polysilane which, in a subsequent pyrolysis, is converted in high yield into a silicon carbide having a silicon-to-carbon ratio near the stoichiometric ratio of SiC, i.e., to silicon carbide having a silicon-to-carbon ratio near 1, and which possesses excellent processability into SiC fibers in particular. The method of the present invention is further also performable in a simple, quick and inexpensive manner, since additional operations, such as the admixture of a sintering additive and/or a subsequent calcining step and/or a subsequent burning can be eschewed since the method of the present invention surprisingly leads even without such additional steps to a polysilane which at most includes a minimal fraction of free carbon. As a result of eschewing the removal of free carbon, the silicon carbide fibers obtained by spinning have an extremely low level of porosity and an excellent mechanical stability, since no dislocations due to the removal of free carbon are created in these fibers. There is moreover also no need for conversion into polycarbosilane.

Without wishing to be tied to any one theory, it is believed that the use of a silane monomer containing at least one aryl group—in addition to silane monomer(s) containing at least one alkenyl group, at least one alkyl group and also at least three halogen atoms attaching to a silicon atom—in the reaction with the alkali metal leads to a polysilane having an improved processability and, in particular, an improved spinnability into a polysilane fiber. Surprisingly, the use of a silane monomer having one or more aryl groups—provided silane monomer(s) having at least one alkenyl group, at least one alkyl group and also at least three halogen atoms attaching to a silicon atom is/are used simultaneously—leads to a polysilane which on pyrolysis leads—despite this silane monomer's low silicon-to-carbon ratio due to the aryl group—to a silicon carbide having a silicon-to-carbon ratio near the stoichiometric ratio of 1. The at least one alkenyl group is also ascribed a beneficial effect on the processability of the polysilane obtained. This group moreover increases the yield of SiC in the later pyrolysis, presumably because the alkenyl group promotes polysilane crosslinking during the pyrolysis. As to free carbon, i.e. carbon which does not attach to silicon carbide by a covalent bond and which would lead to a reduced silicon-to-carbon ratio compared with the stoichiometric ratio, is further only formed in the pyrolysis of alkenyl groups to a reduced extent, if at all. Moreover, the silane monomer having three halogen atoms attaching to a silicon atom is of great importance for the processability and particularly for an excellent pyrolyzability of the polysilane obtained. It is believed in this context that the trifunctionality of this monomer prevents the formation of cyclic silanes which, in the later pyrolysis, would vaporize owing to their low boiling point, leading in the pyrolysis to voids in the material and to lost yield. Finally, the alkyl groups serve as simple-to-provide and inexpensive substituents which favor the formation of nearly stoichiometric silicon-to-carbon ratio in the pyrolysis of the polysilane.

Polysilane in the context of the present invention refers to any silane that has at least 5, preferably at least 10 and more preferably at least 20 interconnected silicon atoms.

Silane monomer in the context of the present invention refers to any silanes other than polysilanes, i.e., to silanes having fewer than 5 silicon atoms, preferably not more than 3 silicon atoms, more preferably not more than 2 silicon atoms and most preferably merely one silicon atom.

According to the present invention, the method for producing the polysilane utilizes at least two silane monomers which by way of structural units contain at least one aryl group, at least one alkyl group, at least one alkenyl group and also at least three halogen atoms attaching to a silicon atom. The individual aforementioned groups may be distributed in any desired manner over the two or more silane monomers used. When four silane monomers are used, for example, they may each have one of the aforementioned four structural units. Alternatively, it is also possible to use three or even only two silane monomers whereof two or three each have at least two of the aforementioned four structural units. Preferably, not just the three halogen atoms but also every one of the other aforementioned structural units, i.e., the at least one aryl group, the at least one alkyl group and also the at least one alkenyl group, each attach directly to a silicon atom of the corresponding silane monomer.

In principle, it is also possible for individual groups of the silane monomers to contain two or even more of the aforementioned four structural units. It is merely by way of example that a styryl group, which contains not only an alkenyl group but also an aryl group, may be mentioned in this context. In such a case, the group meets correspondingly many of the at least four aforementioned criteria, i.e., in the case of a styryl group, the two criteria of at least one aryl group being present and of at least one alkenyl group being present. In such a case, the at least two silane monomers accordingly contain fewer than four different radicals.

In principle, the method of the present invention may utilize one or more silane monomers having one or more than one aryl group of any desired type. However, good results are obtained in particular when the silane monomers used in the reaction have at least one $C_{6-25}$ aryl group, preferably a $C_{6-15}$ aryl group, more preferably a $C_{6-14}$ aryl group, yet more preferably a $C_{6-12}$ aryl group and yet even more preferably a $C_{6-10}$ aryl group. It is most preferable for the reaction to utilize at least one silane monomer having at least one phenyl group as aryl group. It will be appreciated that, within the recited ranges for the number of carbon atoms in the aryl group, only those aryl groups that lead to stable and handleable silane monomers are chosen.

The at least one aryl group which preferably attaches directly to a silicon atom of one of the silane monomers may be an unsubstituted aryl group, such as the aforementioned phenyl group, or a substituted aryl group. In the latter case, the at least one aryl group may be substituted for example with at least one radical selected from the group consisting of linear alkyl radicals, branched alkyl radicals, cyclic alkyl radicals, linear alkenyl radicals, branched alkenyl radicals, cyclic alkenyl radicals, linear alkynyl radicals, branched alkynyl radicals, cyclic alkynyl radicals and any desired combinations of two or more of the aforementioned radicals. The aforementioned substituents may have for example from 1 to 25 carbon atoms, preferably from 1 to 15 carbon atoms, more preferably from 1 to 10 carbon atoms, yet more preferably from 1 to 6 carbon atoms and most preferably from 1 to 4 carbon atoms.

Merely by way of example there may be mentioned as suitable substituents methyl radicals, ethyl radicals, n-propyl radicals, isopropyl radicals, n-butyl radicals, sec-butyl radicals, isobutyl radicals, tert-butyl radicals, vinyl radicals, n-propenyl radicals, isopropenyl radicals, linear butenyl radicals, branched butenyl radicals, ethynyl radicals, propynyl radicals and butynyl radicals, which can be used alone or in any desired combination with one another. Particular preference for use as substituent, if used, is given to methyl radicals, ethyl radicals, n-propyl radicals, isopropyl radicals, n-butyl radicals, sec-butyl radicals, isobutyl radicals, tert-butyl radicals and any desired combination of two or more of the above-itemized radicals.

Even though the use of substituted aryl groups is possible, the particular preference of the present invention is for the use of unsubstituted aryl groups, in particular phenyl groups.

It is proposed, in the development of the concept of the present invention, that the at least one alkyl group which is present as structural unit in the at least two silane monomers and which preferably attaches directly to a silicon atom of one of the silane monomers is a $C_{1-25}$ alkyl group, preferably a $C_{1-15}$ alkyl group, more preferably a $C_{1-10}$ alkyl group, yet more preferably a $C_{1-6}$ alkyl group, yet even more preferably a $C_{1-4}$ alkyl group and yet still even more preferably a $C_{1-3}$ alkyl group. The aforementioned alkyl groups may be cyclic, branched or linear alkyl groups, in which case it is preferable for the at least one alkyl group to be linear. For example, the at least one alkyl group may be a methyl group, an ethyl group, an n-propyl group, an isopropyl group, an n-butyl group, a sec-butyl group, an isobutyl group, a tert-butyl group, an n-pentyl group, a branched pentyl group, a cyclopentyl group, an n-hexyl group, a branched hexyl group, a cyclohexyl group or any desired combination of two or more of the aforementioned groups.

Very particularly good results are obtained when the at least one alkyl group present as structural unit in the at least two silane monomers is an ethyl group or more preferably a methyl group.

It is preferable even in this case for the at least one alkyl group provided as structural unit in the at least two silane monomers to be unsubstituted.

Alternatively, substituted alkyl groups can also be used, in which case the substituents used can be any functional group which a person skilled in the art knows for this purpose. Merely by way of example there may be mentioned in this connection as possible substituents those which are selected from the group consisting of hydroxyl groups, ether groups, amino groups, halogens and any desired combinations of two or more of the aforementioned functional groups.

Nor is the present invention particularly restricted as regards the chemical nature of the at least one alkenyl group which is used as structural unit and which preferably attaches directly to a silicon atom of one of the silane monomers. For example, the at least one alkenyl group may be any desired cyclic, branched or linear $C_{2-25}$ alkenyl group, although good results are obtainable in particular with a $C_{2-15}$ alkenyl group, more preferably a $C_{2-10}$ alkenyl group, yet more preferably a $C_{2-6}$ alkenyl group and yet even more preferably a $C_{2-4}$ alkenyl group. The at least one alkenyl group is most preferably a vinyl group.

All the alkenyl groups itemized above may be substituted or unsubstituted, possible substituents including any examples mentioned above in relation to alkyl groups and aryl groups. When substituted alkenyl groups are used, it is preferable for the at least one alkenyl group to be substituted on at least one carbon atom of the double bond with a $C_{1-25}$ alkyl radical, more preferably with a $C_{1-15}$ alkyl radical, yet more preferably with a $C_{1-10}$ alkyl radical, yet still more preferably with a $C_{1-6}$ alkyl radical and most preferably with a $C_{1-4}$ alkyl radical. Examples of a corresponding substituent are those from the group consisting of methyl radicals, ethyl radicals, n-propyl radicals, isopropyl radicals, n-butyl radicals, isobutyl radicals, sec-butyl radicals, tert-butyl radicals and any desired combinations of two or more of the aforementioned alkyl radicals.

However, it is very particularly preferable for the at least one alkenyl group to be unsubstituted, and most preferable for the at least one alkenyl group to be an unsubstituted vinyl group.

The at least three halogen atoms attaching to a silicon atom of one of the silane monomers may be any desired halogen atoms, i.e., fluorine, chlorine, bromine or iodine, in which case the at least three halogen atoms may be the same or different. For example, a silicon atom of one of the silane monomers may have a fluorine atom, a bromine atom and also an iodine atom attached thereto. However, it is preferable for three identical halogen atoms to attach to a silicon atom of one of the silane monomers, and it is very particularly preferable for the at least three halogen atoms to each be chlorine.

As explained above, the structural units used are preferably unsubstituted groups. Therefore, in a development of the concept of the present invention, it is proposed that at least one of the at least one aryl group, of the at least one alkyl group and of the at least one alkenyl group, preferably at least two of the at least one aryl group, of the at least one alkyl group and of the at least one alkenyl group and more preferably all of the at least one aryl group, of the at least one alkyl group and of the at least one alkenyl group are unsubstituted.

In addition to the four aforementioned structural units, i.e., in addition to the at least one aryl group, to the at least one alkyl group, to the at least one alkenyl group and to the at least three halogen atoms attaching to a silicon atom of one of the silane monomers, at least one of the silane monomers may optionally have one or more hydrogen atoms attaching directly to its silicon atom, i.e., at least one of the silane monomers may optionally have at least one SiH group. Preferably, in this embodiment, only one SiH group is present in the silane monomers. The presence of the SiH group(s) enhances the crosslinkability and thus leads to a more crosslinked polysilane being obtained.

In a particularly preferable embodiment of the present invention, the step of reacting utilizes at least three silane monomers having the following general formulae (1) to (3):

$$R^1SiX_3 \qquad (1)$$

$$R^2R^3SiX_2, \qquad (2)$$

and $$R^4R^5SiX_2 \qquad (3)$$

where:
- $R^1$ is an aryl group,
- $R^2$ is an alkenyl group,
- $R^3$, $R^4$ and $R^5$ are the same or different and are each an alkyl group or H, with the proviso that at least one of $R^3$, $R^4$ and $R^5$ is an alkyl group, and
- X at each occurrence is a halogen atom.

The groups used in the above general formulae, i.e., aryl groups, alkenyl groups, alkyl groups and halogen atoms, may be those which are recited in detail in the above embodiments. Any halogen atoms can accordingly be used, in which case the individual halogen atoms can be identical or different. The halogen atoms are preferably all chlorine atoms. Aryl group $R^1$ may accordingly be in particular any substituted or unsubstituted $C_{6-25}$ aryl group, preferably $C_{6-18}$ aryl group, more preferably $C_{6-14}$ aryl group, yet more preferably $C_{6-12}$ aryl group and most preferably $C_{6-10}$ aryl group. Preferably, aryl group $R^1$ is an unsubstituted aryl group and most preferably a phenyl group. Alkenyl group $R^2$ will accordingly be in particular any substituted or unsubstituted, cyclic, branched or linear $C_{2-25}$ alkenyl group, preferably $C_{2-15}$ alkenyl group, more preferably $C_{2-10}$ alkenyl group, yet more preferably $C_{2-6}$ alkenyl group or most preferably $C_{2-4}$ alkenyl group. Preferably, alkenyl group $R^2$ is an unsubstituted linear alkenyl group or most preferably a vinyl group. Alkyl groups $R^3$, $R^4$ and $R^5$ may each accordingly be in particular any substituted or unsubstituted, cyclic, branched or linear $C_{1-25}$ alkyl group, preferably $C_{1-15}$ alkyl group, more preferably $C_{1-10}$ alkyl group, yet more preferably $C_{1-6}$ alkyl group, yet still more preferably $C_{1-4}$ alkyl group and most preferably $C_{1-3}$ alkyl group. Preferably, alkyl groups $R^3$, $R^4$ and $R^5$ are each an unsubstituted linear alkyl group, more preferably an ethyl group and most preferably a methyl group.

Particularly good results are obtained with the above embodiment in particular when the individual radicals in general formulae (1) to (3) are each as follows:
- $R^1$ is a phenyl group,
- $R^2$ is a vinyl group,
- each of $R^3$, $R^4$ and $R^5$, which are the same or different, is an alkyl group or H, with the proviso that at least one of $R^3$, $R^4$ and $R^5$ is an alkyl group, and
- X at each occurrence is a chlorine atom.

In the above embodiment, alkyl groups $R^3$, $R^4$ and $R^5$ are preferably $C_{1-22}$ alkyl groups, more preferably $C_{1-12}$ alkyl groups, yet more preferably $C_{1-6}$ alkyl groups, yet still more preferably $C_{1-4}$ alkyl groups, yet still even more preferably $C_{1-3}$ alkyl groups, yet still further even more preferably $C_{1-4}$ alkyl groups and most preferably methyl groups. It is therefore particularly preferable when the individual radicals in general formulae (1) to (3) are each as follows:
- $R^1$ is a phenyl group,
- $R^2$ is a vinyl group,
- each of $R^3$, $R^4$ and $R^5$, which are the same or different, is a $C_{1-22}$ alkyl group, preferably a $C_{1-12}$ alkyl group, more preferably a $C_{1-6}$ alkyl group, yet more preferably a $C_{1-4}$ alkyl group, yet still more preferably a $C_{1-3}$ alkyl group, yet still even more preferably a $C_{1-4}$ alkyl group and most preferably a methyl group, and
- X at each occurrence is a chlorine atom.

In a very particularly preferable embodiment of the present invention, the step of reacting uses phenyltrichlorosilane, dichloromethylvinylsilane and dichlorodimethylsilane as silane monomers, i.e., three silane monomers conforming to general formulae (1) to (3):

$$R^1SiX_3, \quad (1)$$

$$R^2R^3SiX_2 \quad (2)$$

and $$R^4R^5SiX_2, \quad (3)$$

where:
- $R^1$ is a phenyl group,
- $R^2$ is a vinyl group,
- $R^3$, $R^4$ and $R^5$ are each a methyl group, and
- X at each occurrence is a chlorine atom.

The three silane monomers above may each be used alone or optionally together with one or more additional silane monomers. However, to attain good processability for the polysilane obtained therefrom and to attain an at least nearly stoichiometric Si:C ratio after pyrolysis of the polysilane obtained therefrom, preferably only the three aforementioned silane monomers, i.e., phenyltrichlorosilane, dichloromethylvinylsilane and dichlorodimethylsilane, are used in the reaction.

In principle, the individual silane monomers can be used in the reaction in any desired ratio relative to one another. In the above embodiments where at least three silane monomers of general formulae (1) to (3) are used, it is preferable for the attainment of good processability on the part of the polysilane obtained therefrom and the attainment of an at least nearly stoichiometric Si:C ratio after pyrolysis of the polysilane obtained therefrom that, in the reaction, the amount-of-substance fraction of the silane monomer of general formula (1) is from 15 to 30 mol %, the amount-of-substance fraction of the silane monomer of general formula (2) is from 5 to 40 mol % and the amount-of-substance fraction of the silane monomer of general formula (3) is from 43 to 66 mol % based on the sum total of these three amount-of-substance amounts. When at least one of the silane monomers has at least one SiH group, the proportion of this silane monomer is preferably in the range from 10 to 40 mol %.

Particularly good processability and especially spinnability for the product polysilane and also an Si:C ratio particularly near to 1 after pyrolysis of the polysilane obtained therefrom is surprisingly obtained when in the above embodiments where at least three silane monomers of the general formulae (1) to (3) are used, in the reaction, the amount-of-substance fraction of the silane monomer of general formula (1) is from 16 to 20 mol %, the amount-of-substance fraction of the silane monomer of general formula (2) is from 25 to 30 mol % and the amount-of-substance fraction of the silane monomer of general formula (3) is from 53 to 59 mol % based on the sum total of these three amount-of-substance amounts. When at least one of the silane monomers has at least one SiH group, the proportion of this silane monomer is preferably in the range from 25 to 30 mol %.

Any alkali metals can be used in the reaction, such as lithium, sodium, potassium, rubidium, cesium, francium and any desired combinations of two or more of the aforementioned metals. However, it is preferable for the step of reacting to utilize sodium, potassium, a mixture of sodium and potassium or an alloy of sodium and potassium. The aforementioned metals can all be used in liquid form, i.e., as a melt, or as a solid suspended in a solvent. However, it is preferable for the alkali metal to be used in liquid form, i.e., as a melt, and the melt is preferably finely dispersed in an organic solvent using a suitable stirring means, for example a paddle stirrer. This embodiment provides a particularly homogeneous emulsion, which is preferable to a more heterogeneous suspension. It is particularly preferable in this connection that the alkali metal used is sodium, a mixture of sodium and potassium or an alloy of sodium and potassium.

One advantage to using a mixture/alloy of sodium and potassium is that adding the potassium lowers the melting point of the sodium—to below room temperature provided the appropriate amount of potassium is added. Therefore, using a mixture or alloy of sodium and potassium makes possible the use of liquid alkali metal even at room temperature. In this embodiment, the mixture/alloy preferably contains just enough potassium to lower the melting point of sodium to a desired value, since, in the reaction, potassium, unlike sodium, leads to unwanted secondary reactions with the double bond of the alkenyl group.

It is particularly preferable to use sodium as the sole alkali metal in the reaction.

In the step of reacting, the amount of alkali metal is preferably from 0.9 to 1.5 and more preferably from 1.0 to 1.5 relative to the amount of halogen atoms in the silane monomers.

It is proposed, in a development of the concept of the present invention, that the step of reacting be carried out in at least one organic solvent, wherein the at least one organic solvent is preferably selected from the group consisting of diethyl ether, tetrahydrofuran, 1,4-dioxane, benzene, toluene, xylene and any desired combinations of two or more of the aforementioned components. Tetrahydrofuran and toluene are each particularly suitable and a mixture of tetrahydrofuran and toluene is very particularly preferable.

In principle, the step of reacting can be carried out at any desired temperature where there is a sufficiently high rate of reaction. However, for the above reasons, viz., attainment of a particularly homogeneous dispersion of alkali metal in the solvent containing the silane monomers, it is preferable for the reaction to be carried out at a temperature at which the alkali metal is in the form of a melt. The reaction temperature is therefore preferably at least 97.7° C. in the case of sodium and at least 63.4° C. in the case of potassium. When a mixture/alloy of sodium and potassium is used, the melting point lowering makes it possible to reduce the reaction temperature correspondingly. Depending on the particular alkali metal used, the step of reacting may therefore be carried out at a temperature of from 0 to 200° C., preferably from 20 to 180° C., more preferably from 60 to 160° C., yet more preferably from 80 to 160° C., yet still more preferably from 90 to 140° C. and most preferably from 98 to 120° C.

To prevent secondary reactions and particularly oxidative reactions as far as possible, a development of the concept of the present invention proposes that the reaction be carried out under an inert gas, such as nitrogen or argon.

After the reaction, the undissolved constituents, which inter alia contain unreacted alkali metal, are separated off by filtration, so the target polysilane is obtained in the filtrate and may be isolated therefrom by evaporating the solvent. Owing to the high yield of soluble polysilane, the reaction yield of the method according to the present invention is high.

The present application for a patent further provides a polysilane that is obtainable using the method described above. A polysilane of this type is notable for a comparatively high molar mass and is surprisingly also pyrolyzable to SiC having a nearly stoichiometric Si:C ratio.

In one preferred embodiment of the present invention, the polysilane of the present invention includes from 0.01 to 0.98 alkyl groups, from 0.01 to 0.96 alkenyl groups and from 0.01 to 0.20 aryl groups, based on the sum total of the aforementioned groups in the polysilane being all together 1.00. The polysilane particularly preferably includes from 0.50 to 0.98 alkyl groups, from 0.01 to 0.30 alkenyl groups and from 0.01 to 0.20 aryl groups. Particularly good results, especially with regard to the stoichiometry to be obtained between silicon and carbon following the pyrolysis to SiC, are obtained when the polysilane includes from 0.77 to 0.96 alkyl groups, from 0.02 to 0.11 alkenyl groups and from 0.02 to 0.12 aryl groups and especially when the polysilane includes from 0.84 to 0.92 alkyl groups, from 0.05 to 0.11 alkenyl groups and from 0.02 to 0.06 aryl groups.

Since, as explained above in relation to the method, the alkyl groups are preferably methyl groups, the alkenyl groups are preferably vinyl groups and the aryl groups are preferably phenyl groups, it is particularly preferable for the polysilane of the present invention to include from 0.01 to 0.98 methyl groups, from 0.01 to 0.96 vinyl groups and from 0.01 to 0.20 phenyl groups as substituents. It is very particularly preferable for the polysilane to include from 0.50 to 0.98 methyl groups, from 0.01 to 0.30 vinyl groups and from 0.01 to 0.20 phenyl groups, it is still further preferable for the polysilane to include from 0.77 to 0.96 methyl groups, from 0.02 to 0.11 vinyl groups and from 0.02 to 0.12 phenyl groups and most preferable for the polysilane to include from 0.84 to 0.92 methyl groups, from 0.05 to 0.11 vinyl groups and from 0.02 to 0.06 phenyl groups. These numerical values, as described in the preceding paragraph, are based on the combined number of the aforementioned substituents being 1.00. These numbers thus indicate the molar ratio between the substituents referred to. This relative number of substituents in the polysilane of the present invention is easily determined via $^1$H NMR spectroscopy for example. In $^1$H NMR spectroscopy, the ratio of the different hydrogen signals is used to compute the ratio between the different substituents, giving the molar fraction for each substituent.

Preferably, the polysilane of the present invention has a number-averaged molar mass Mn of 600 to 4000 g/mol, preferably of 700 to 2000 g/mol, more preferably of 800 to 1500 g/mol and most preferably of 900 to 1200 g/mol. In the present invention, the number-averaged molar mass is determined by GPC, and this in accordance with German standard specification DIN 55672.

The present invention further provides a shaped article in silicon carbide. The shaped article is obtainable by pyrolyzing the polysilane of the present invention. A silicon carbide of this type is notable for a nearly stoichiometric Si:C ratio, i.e., for a low level of free carbon. The shaped article may be a fiber, a matrix material or the like.

In principle, the pyrolysis can be carried out in any manner known to a person skilled in the art and with any temperature profile. Good results, however, are obtained in particular when the pyrolysis is carried out in the absence of oxygen, i.e., in an inert gas atmosphere, such as nitrogen, such that the maximum temperature is from 400 to 1200° C., preferably from 600 to 1000° C. and more preferably from 800 to 900° C.

Optionally, the polysilane may be cured before the pyrolysis, in which case the curing may be effected using, for example, UV light and/or a heat treatment, which may be part of the pyrolysis.

It is proposed, in a development of the concept of the present invention, that the heating rate in the pyrolysis be set to a value between 0.1 and 200 K/min, preferably between 0.5 and 50 K/min, more preferably between 0.75 and 10 K/min and most preferably to a value of about 1.0 K/min. The conversion of the polysilane to the SiC is concluded at from 400 to 500° C. However, the treatment at a higher temperature is necessary in order to achieve the desired formation of microstructure.

As explained above, the silicon carbide of the shaped article according to the invention is notable for a nearly stoichiometric Si:C ratio, i.e., for a low level of free carbon. The ratio of the amount-of-substance amounts of silicon to carbon in the silicon carbide is preferably in the range from 0.75 to 1.25, more preferably in the range from 0.8 to 1.20, yet more preferably in the range from 0.85 to 1.15, yet still more preferably in the range from 0.9 to 1.0 and most preferably in the range from 0.95 to 1.0. In the present invention, the amount-of-substance ratio of silicon to carbon is determined by elemental analysis. The carbon content is determined in the present invention according to the principle of combusting a sample and analyzing the combustion gases using infrared absorption. In this procedure, the sample to be analyzed is inductively heated to temperatures between 1250° C. and 1400° C. in a high-frequency oven and combusted by supply of oxygen, the $CO_2$ formed being passed through an infrared cell. The intensity of the absorption of the corresponding band can be used to infer the amount. The oxygen content is also determined according to the principle of combusting a sample and analyzing the combustion gases using infrared absorption. Helium is used as carrier gas. The sample to be analyzed is inductively heated to temperatures between 1250° C. and 1400° C. in a high-frequency oven, the oxygen in the sample reacts with the graphite crucible in which the sample is located, and the resulting $CO_2$ and CO is passed through an infrared cell. The intensity of the absorption of the corresponding band can be used to infer the amount. Since there are no further elements in the sample, the silicon content can be obtained by subtracting the previously obtained carbon and oxygen values from 100%.

In one preferred embodiment of the present invention, the shaped article is a silicon carbide fiber. The diameter of the fiber(s) in this embodiment is preferably in the range from 1 to 100 µm, more preferably in the range from 5 to 50 µm, even more preferably in the range from 10 to 20 µm and most preferably in the range from 10 to 15 µm. These fibers are obtainable in a simple manner by spinning and then pyrolyzing the above-described polysilane of the present invention. The spinning in question can be done with a melt of the polysilane or with a solution containing the polysilane. In the latter case, useful solvents include, for example, tetrahydrofuran, xylene and/or toluene.

Particularly when the shaped article is an SiC fiber, the crystallinity of the shaped article is preferably from 20 to 80%, more preferably from 40 to 70% and most preferably from 50 to 60%. However, it is also possible for the shaped article to be wholly amorphous or wholly crystalline, so crystallinities from 0 to 100% are possible according to the present invention.

In a further preferred embodiment of the present invention, the grain size of the SiC of the shaped article is in the range from 0 to 20 µm, preferably from 0.01 to 15 µm, more preferably from 0.03 to 10 µm, yet more preferably from 0.05 to 5 µm and most preferably from 0.1 to 2 µm.

Finally, as will be known in principle, a sizing agent may be provided to the SiC fiber.

The present invention further provides a composite material and especially a fiber composite material comprising at least one above-described shaped article in silicon carbide. In this fiber composite material, the fibers or the matrix may be composed of silicon carbide, although preferably the fibers and the matrix are both composed of silicon carbide.

The fibers may further be in the form of non-crimp fabrics, fiber mats, wovens, knits, nonwovens and/or felts, of which non-crimp fabrics and/or fiber mats are preferable.

To produce the composite material of the present invention, fibrous structures comprising SiC fibers obtained as described above may be impregnated with polysilane and then pyrolyzed as described above. Optionally, a cure may be effected between impregnation and pyrolysis, in which case curing may be effected using for example UV light and/or by heat treatment. Thereafter, the body thus obtained may be impregnated with polysilane one or more times, cured and pyrolyzed.

Owing to its outstanding properties, in particular its outstanding high temperature resistance and high hardness, the shaped article and/or fiber composite material of the present invention is particularly useful for applications where the material is exposed to high temperatures and oxidative conditions, for example in lightweight construction, the electrical industry, aerospace, motor vehicle construction and aircraft construction. Owing to the production method of the present invention being less costly, especially the use of the shaped article and/or fiber composite material in the present invention as a material for clutch or brake disks is preferable.

The present invention will now be described with reference to exemplary embodiments which explain and described the invention, but do not limit the present invention.

EXAMPLES

Example 1

An apparatus for performing chemical syntheses by using the standard Schlenk technique, said apparatus comprising a three-neck flask equipped with a reflux condenser, a dropping funnel with pressure equalizer and a KPG stirrer, was evacuated and filled with argon. A mixture of 102 ml of tetrahydrofuran, 610 ml of toluene and 112.4 g of sodium was introduced into the three-neck flask as an initial charge at room temperature under argon. The dropping funnel was charged, likewise under argon, with 57 ml of phenyltrichlorosilane, 76 ml of dichloromethylvinylsilane and 152 ml of dimethyldichlorosilane. Stirrer speed was adjusted to 250 revolutions per minute and the initial charge in the three-neck flask was heated with an oil bath to a temperature of about 100° C. In the process, an emulsion of molten sodium in tetrahydrofuran and toluene was formed. This emulsion was admixed at 100° C. with the mixture of silanes from the dropping funnel in the course of about 50 min at a drop rate of 5.7 ml/min, a blue color indicating the onset of the reaction. On completion of the admixture, the reaction mixture was stirred at 100° C. for a further 2 hours and then allowed to cool down to room temperature. The suspension obtained was filtered through a protective gas frit having a pore size of 10 µm under argon, leaving behind on the frit a residue of sodium chloride, unreacted sodium and the insoluble fraction of the polysilane formed in the course of the reaction, and the residue was washed with 160 ml of toluene. The filtrate obtained contained the soluble fraction of the polysilane formed, and the solvents were speedily removed from it in vacuo to obtain the soluble fraction of the polysilane in a yield of 81%. The number-averaged molar mass Mn was found by gel permeation chromatography to be 1110 g/mol.

NMR determination revealed that the polysilane obtained contained the following relative amounts of side chain groups:

88.8 mol % of methyl groups,
8.0 mol % of vinyl groups, and
3.2 mol % of phenyl groups.

The polysilane obtained was dissolved in tetrahydrofuran and spun from the solution into a fiber having a diameter of on average 35 µm. The fiber obtained was then dried in argon at room temperature and subjected to a pyrolysis. To this end, the fiber was placed in an oven and heated to a temperature of 150° C. at a heating rate of 1 K/min. The temperature of 150° C. was maintained for a period of 30 min. Further heating to a temperature of 800° C. was done at a heating rate of 5 K/min. The holding time at 800° C. was 0 min, before cooling down to room temperature at a cooling rate of 10 K/min to obtain a silicon carbide fiber having a diameter of on average 15 µm and also an amount-of-substance ratio, as determined by elemental analysis, of 0.92 for silicon to carbon.

Example 2

A polysilane was produced as described in Example 1 except that 95 ml of phenyltrichlorosilane, 19 ml of dichloromethylvinylsilane and 171 ml of dichlorodimethylsilane were used. The soluble fraction of the polysilane was obtained in a yield of 84%. The number-averaged molar mass Mn determined by gel permeation chromatography was 969 g/mol.

The polysilane obtained was spun into a fiber and pyrolyzed as described in Example 1. The silicon carbide fiber obtained had an amount-of-substance ratio, as determined by elemental analysis, of 0.85 for silicon to carbon.

Example 3

A polysilane was produced as described in Example 1 except that 58.4 ml of phenyltrichlorosilane, 79.8 ml of dichloromethylvinylsilane and 146.8 ml of dichlorodimethylsilane were used. The soluble fraction of the polysilane was obtained in a yield of 76%. The number-averaged molar mass Mn determined by gel permeation chromatography was 1570 g/mol.

The polysilane obtained was likewise spun into a fiber and pyrolyzed as described in Example 1. The silicon carbide fiber obtained had an amount-of-substance ratio, as determined by elemental analysis, of 0.96 for silicon to carbon.

Comparative Example 1

A polysilane was produced as described in Example 1 except that 114 ml of phenyltrichlorosilane and 171 ml of dichlorodimethylsilane were used. The soluble fraction of the polysilane was obtained in a yield of 90%. The number-averaged molar mass Mn determined by gel permeation chromatography was 941 g/mol.

The silicon carbide obtained had an amount-of-substance ratio, as determined by elemental analysis, of 0.48 for silicon to carbon.

Comparative Example 2

A polysilane was produced as described in Example 1 except that 285 ml of dichloromethylvinylsilane were used. The soluble fraction of the polysilane was obtained in a yield of 46%. The number-averaged molar mass Mn determined by gel permeation chromatography was 1030 g/mol.

The polysilane obtained could not be spun into a fiber as described in Example 1. The silicon carbide obtained had an amount of substance ratio, as determined by elemental analysis, of 0.97 for silicon to carbon.

Comparative Example 3

A polysilane was produced as described in Example 1 except that 285 ml of phenyltrichlorosilane were used. The soluble fraction of the polysilane was obtained in a yield of 100%. The number-averaged molar mass Mn determined by gel permeation chromatography was 1720 g/mol.

The polysilane obtained was spun into a fiber as described in Example 1. For this, the fiber was placed in an oven and heated to a temperature of 300° C. at a heating rate of 1 K/min. The temperature of 300° C. was maintained for a period of 180 min. Further heating to a temperature of 800° C. was done at a heating rate of 5 K/min. The holding time at 800° C. was 0 min, before cooling down to room temperature at a cooling rate of 10 K/min.

The silicon carbide fiber obtained had a diameter of 13.3 µm and an amount-of-substance ratio, as determined by elemental analysis, of 0.36 for silicon to carbon.

Comparative Example 4

A polysilane was produced as described in Example 1 except that 285 ml of dimethyldichlorosilane were used. The soluble fraction of the polysilane was obtained in a yield of 87%. Gel permeation chromatography could not be used to determine any values, since the polysilane could no longer be taken up in tetrahydrofuran.

The polysilane obtained was neither spinnable nor pyrolyzable.

The invention claimed is:

1. A method for producing a polysilane, the method comprising:
reacting (i) at least two silane monomers and (ii) at least one alkali metal, the silane monomers containing the following structural units:
at least one aryl group;
at least one alkyl group;
at least one alkenyl group; and
at least three halogen atoms, wherein at least three of the halogen atoms attach to a silicon atom of one of the silane monomers;
the reacting step including utilizing three silane monomers having the following general formulae (1) to (3):

$$R^1SiX_3 \qquad (1)$$

$$R^2R^3SiX_2 \qquad (2)$$

$$R^4R^5SiX_2 \qquad (3)$$

where:
$R^1$ is an aryl group;
$R^2$ is an alkenyl group;
$R^3$, $R^4$ and $R^5$ are the same or different and are each an alkyl group or H, with the proviso that at least one of $R^3$, $R^4$ and $R^5$ is an alkyl group; and
each X is a halogen atom.

2. The method according to claim 1, wherein the silane monomers are selected from the group consisting of phenyltrichlorosilane, dichloromethylvinylsilane and dimethyldichlorosilane.

3. The method according to claim 1, wherein, based on a sum total of the following three amount-of-substance amounts:
an amount-of-substance fraction of the silane monomer of the general formula (1) is from 15 to 30 mol %;
an amount-of-substance fraction of the silane monomer of the general formula (2) is from 5 to 40 mol %; and
an amount-of-substance fraction of the silane monomer of the general formula (3) is from 43 to 66 mol %.

4. A shaped article of silicon carbide obtained by pyrolyzing a polysilane according to claim 3, wherein a ratio of silicon to carbon in the silicon carbide lies within a range from 0.75 to 1.25.

5. The shaped article according to claim 4, wherein the ratio of silicon to carbon lies in the range from 0.8 to 1.20, or the ratio of silicon to carbon lies in the range from 0.85 to 1.15, or the ratio of silicon to carbon lies in the range from 0.9 to 1.0, or the ratio of silicon to carbon lies in the range from 0.95 to 1.0.

6. A fiber composite material, comprising at least one shaped article in silicon carbide according to claim 4, the composite material containing fibers of silicon carbide and a matrix material.

* * * * *